US006544183B2

(12) United States Patent
Thorn Leeson et al.

(10) Patent No.: US 6,544,183 B2
(45) Date of Patent: Apr. 8, 2003

(54) METHOD FOR IMAGING SKIN SURFACE INTERCELLULAR AND INTRACELLULAR STRUCTURE USING A COMPOUND TO ENHANCE CONTRAST

(75) Inventors: Daniel Thorn Leeson, Hoboken, NJ (US); Krishna Kumar Subramanyan, Edgewater, NJ (US); Kavssery Parameswaran Ananthapadmanabhan, Highland Mills, NY (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/920,793

(22) Filed: Aug. 2, 2001

(65) Prior Publication Data

US 2003/0028099 A1 Feb. 6, 2003

(51) Int. Cl.[7] .................................................. A61B 8/00
(52) U.S. Cl. ........................ 600/458; 600/437; 324/308
(58) Field of Search ................................. 600/437, 443, 600/444–447, 458; 128/916; 367/7; 324/309, 318, 308

(56) References Cited

U.S. PATENT DOCUMENTS 5,526,816 A * 6/1996 Arditi .......................... 600/458
6,121,775 A * 9/2000 Pearlman ..................... 324/300
6,375,617 B1 * 4/2002 Fraser ......................... 128/916

OTHER PUBLICATIONS

International Journal of Cosmetic Science, 2001, 23, pp. 121–126, "Skin Surface Patterns of Xerotic Legs: The Flexural and Accretive Types", Pierard–Franchimont et al.
J. Cosmet. Sci., 52, pp. 91–102 (Mar.–Apr. 2001) "Skin Optics Revisited by In Vivo Confocal Microscopy: Melanin and Sun Exposure", Corcuff et al.
The Journal of Investigative Dermatology, vol. 113, No. 3, Sep., 1999, pp. 293–303, "In Vivo Confocal Scanning Laser Microscopy of Human Skin II: Advances in Instrumentation and Comparison With Histology", Rajadhyaksha et al.

* cited by examiner

Primary Examiner—Francis J. Jaworski
Assistant Examiner—Maulin Patel
(74) Attorney, Agent, or Firm—Ronald A. Koatz

(57) ABSTRACT

The present invention relates to methods to image the skin surface in order to view intercellular and intracellular structure. In particular, the invention relates to use of a compound (e.g., fluorescent dye) to enhance contrast and obtain better imaging.

6 Claims, 4 Drawing Sheets

METHOD FOR IMAGING SKIN SURFACE INTERCELLULAR AND INTRACELLULAR STRUCTURE USING A COMPOUND TO ENHANCE CONTRAST

FIELD OF THE INVENTION

The present invention relates to methods to image the skin surface in order to view intercellular and intracellular structure. In particular, the invention relates to use of a compound (e.g., fluorescent dye) to enhance contrast and obtain better imaging.

BACKGROUND OF THE INVENTION

Methods, especially in vivo methods, for imaging both the skin surface as well as deeper skin layers at a wide range of lateral resolutions are available. For example, in vivo confocal microscopy is capable of imaging skin at sufficient lateral and axial resolution and with sufficient contrast to distinguish individual skin cells below the skin surface (versus on the skin surface as disclosed by method of the subject invention).

In In vivo Confocal Scanning Laser Microscopy of Human Skin II: Advances in Instrumentation and Comparison With Histology, M. Rajadhyaksha et al. J. Invest. Dermatol. 113 (1999) 293, images are shown of various skin layers, from the skin surface to the dermis. Individual skin cells at the skin surface can be identified but the overall contrast at the surface is poor. Further, the confocal scanning technique is completely different than the dye technique of the subject invention in that it uses a completely different source of contrast.

As far as applicants are aware, a technique using a compound (e.g., a fluorescent dye) for imaging skin surface at the cellular level in vivo is unknown.

BRIEF DESCRIPTION OF THE INVENTION

The present invention relates to a preferably in vivo method to image the intercellular and intracellular structure of the skin surface using a technique to enhance contrast.

The present invention is believed to represent a novel way for making such in vivo measurement.

In the embodiment of the present invention, the intercellular and intracellular structure of the skin surface is imaged by choosing a desired spot on the subject's body; applying a desired amount of a contrast enhancing compound (e.g., fluorescent dye) to the site; taking a stack or multiplicity of images (e.g., fluorescence images) at different focal planes (for example 1 to 1000, preferably 1–100); and, if necessary, performing a maximum intensity rendering of the resulting stack of images.

More specifically, the invention comprises a method to image the intercellular and intracellular structure of the skin surface comprising:

1. choosing a desired site, typically circular, with a diameter of 0.5", although it should be understood that the site can be larger or smaller or differently shaped, on the body of a subject;
2. applying a contrast-enhancing compound to the chosen area; in principal such compound can be any compound which absorbs heterogeneously at the skin surface and can be detected by appropriate imaging tool; typically this would be a fluorescent dye;
3. acquiring a stack or multiplicity of images (typically multiple fluorescent images) of an area, typically 0.01× 0.01" in size but the area can be either smaller or larger, varying the focal plane over a range from just above the highest point to just below the lowest point of the surface area that is imaged, typically in steps of 2 $\mu$m, although the step size can be smaller or larger;
4. reconstructing the resulting multiple images into a single image that shows all the cells at the skin surface in focus (or, if a single image is possible, such reconstruction of multiple images is not necessary), regardless of any skin texture, by performing a maximum intensity rendering of the stack of images; and
5. if desired, repeating steps 3 and 4 to obtain additional images within the chosen body site.

BRIEF DESCRIPTION OF THE FIGURES

FIG. 2 displays two images. The image on the left is a single image out of a stack of images of the same skin surface area taken at different axial positions of the focal plane. The image on the right is the result of a maximum intensity rendering of the stack of images that the image on the left was taken from.

FIG. 3 displays vertical cross sections, along the xz- and yz-planes, of the same stack of images that the single image and maximum intensity rendering shown in FIG. 2 were taken from.

DETAILED DESCRIPTION OF THE INVENTION

Figure 1:
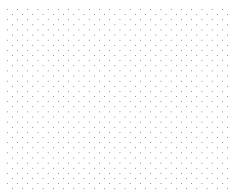
FIG. 1 displays two images of the exact same skin surface area. The image on the left is the reflected light image, while the image on the right is a fluorescence image after topical application of fluorescein. The cells can be observed on the enhanced image at right.
Figure 1:
Figure 1:
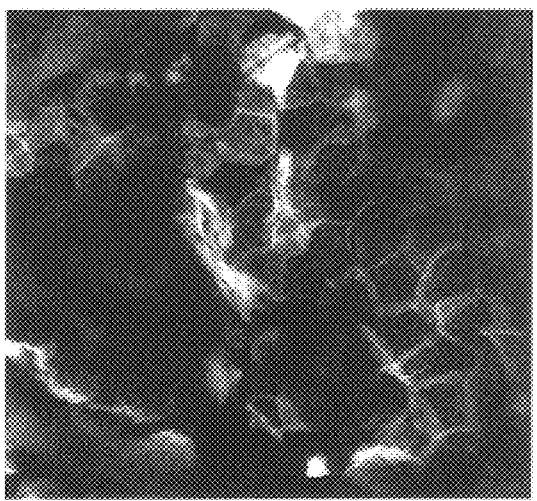

The present invention relates to a preferably in vivo method for imaging the intercellular and intracellular structure of the skin surface. The method is also applicable ex vivo.

Specifically, the invention provides a method for imaging the skin surface in vivo comprising:

1. choosing a desired site, typically circular with a diameter of 0.5" but the site can be either larger or smaller or differently shaped, on the body of a subject (in theory, an arm or entire body can be stained, preferably, however, from 0.1 to 12");
2. applying a contrast enhancing compound such as fluorescent dye (typically fluorescein or any other dye that yields enhanced cellular contrast relative to a reflectance image of the skin surface and that is predominantly absorbed by the uppermost layer of skin cells), typically from an aqueous solution or by any other desired method of topical application, to the chosen area;
3. acquiring a stack or multiplicity of the images (e.g., fluorescence images) of an area (theoretically, single image may be used), typically 0.01×0.01" in size, although the area can be either smaller or larger, at different focal planes, ranging from just above the highest point to just below the lowest point of the skin surface within the area that was chosen, typically in steps of 2 $\mu$m, although the step size can be smaller or larger (typically range is 0.1 to 100 $\mu$m, preferably 1 to 25 $\mu$m);
4. reconstructing the resulting stack of images into a single image (if more than one image used) that shows all the cells at the skin surface in focus, regardless of any skin texture or whether the skin is parallel to the focal plane of the imaging objective that is used, by performing a maximum intensity rendering of the stack of images;

5. if desired, repeating steps 3 and 4 to obtain additional images within the chosen body site.

Each of the process steps is discussed in more detail below and in the examples.

As noted, the first step in the method for imaging skin intercellular and intracellular structure according to the subject invention is to choose a desired spot on the subject suitable for imaging.

The method is applicable to any body site that is suitable for staining with a contrast enhancing compound (e.g., fluorescent dye) and that is suitable for imaging with the imaging instrument that is used in the subsequent step.

In the second step of the invention a contrast-enhancing compound (e.g., fluorescent dye) is applied to the body site that was chosen in the first step.

The size or shape of the site that the compound (e.g., dye) is applied to is determined by the method of application and is limited only by what is considered practical. There is no fundamental limit to the size or shape of the area other than it has to cover the area that is imaged in the subsequent step.

The only requirement for the compound that is applied is that the intercellular contrast, i.e. the ability to identify and determine the outline of individual cells from an image of the skin surface, or the intracellular contrast, i.e. the ability to identify and determine the outline of features within individual cells, when taking images (e.g., fluorescence images), is enhanced relative to when ordinary reflectance images are taken of the same surface. Typically, contrast in fluorescence images, for example, of the skin surface arises from heterogeneous absorbance of the fluorescent dye within individual cells on the surface or between cells. For instance, a certain fluorescent dye may be preferentially absorbed in the outer regions or the cells while another may be preferentially absorbed in the lipid containing regions between cells. Alternatively, a certain dye may be absorbed in different amounts by different cells on the surface. Another possible source of contrast is inhomogenites in the microenvironment around the dye at the surface of the skin.

To further enhance contrast, combinations of compound (e.g., dyes) may be used, combined either with or without obtaining the images (e.g., fluorescence images) at different excitation or emission wavelengths and subsequently combining the resulting images.

Examples of dyes which may used include fluorescein, pyranine, and fluorescein octadecyl ester.

If a maximum intensity rendering is used to reconstruct the intercellular and intracellular structure of a textured skin surface into a single image, an additional requirement is that the dye, depending on the method by which it is applied, is predominantly absorbed by the surface layer (e.g., uppermost layer) of skin cells and exhibits no significant penetration, relative to the amount that is absorbed by the uppermost layer, into the deeper layers. In practice, therefore, the dyes almost always must be non-penetrating dyes (e.g., under conditions of application).

There are no restrictions in the method by which the fluorescent dye is applied or the duration of application other than that it can be reasonably applied in vivo. If the method is applied ex vivo no restrictions exist. A typical method of applying the fluorescent dye is to soak the skin with a solution of the dye.

In the third step of the invention, a stack or multiplicity of images (e.g., fluorescent images) at different axial positions of the focal plane is acquired. In principal, a single image may be used.

In principle, there are no restrictions in the size or shape of the area that is imaged other than that it should be contained within the area that the compound (e.g., fluorescent dye) is applied to. If the method is used to image the intercellular structure of the skin surface, the area that is imaged should at least be larger that the typical size of a skin cell at the skin surface, which is of the order of 10–40 $\mu$m.

A requirement for the instrument that is used to acquire the images is that it has a lateral resolution that is approximately an order of magnitude smaller than the size of a typical cell at the skin surface, or better. That is, it can clearly resolve skin cells.

If a maximum intensity rendering is used to reconstruct the intercellular and intracellular structure of a textured skin surface into a single image, an additional requirement is that the axial resolution of the instrument is approximately an order of magnitude smaller than the typical length scale associated with the surface texture of the surface to be measured, or better. Also in this case, the instrument should have the capability of taking stacks of images at different axial positions of the focal plane.

Furthermore, the instrument should be applicable in vivo.

An example of an instrument that meets these criteria is an in vivo confocal scanning fluorescence microscope.

To be able to reconstruct the stack of images into a single image that shows all the skin cells on the surface in focus, the stack should start just above the highest point on the skin surface and end just below the lowest point of the skin surface area to be imaged.

In the fourth step of the invention (if required), the stack of images is reconstructed into a single image by performing a maximum intensity rendering of the stack of images.

This step is required when the area of the skin surface that is imaged exhibits texture or, in the case of a flat surface, when the skin surface is not parallel with the focal plane of the imaging instrument.

The maximum intensity rendering searches through the stack of images to find which image within the stack displays the maximum intensity at a certain pixel position. Subsequently, it displays that particular intensity at that particular pixel position in the rendered two-dimensional image. Since it is a requirement that the compound is predominantly absorbed by the surface layer of skin cells, for a given pixel position, the pixel with highest intensity is always found at the image within the stack where the focal plane of the imaging instrument overlapped with the skin surface. Consequently, the result of the maximum intensity rendering is a two-dimensional image that displays all the surface cells in focus regardless of skin texture or, in the case of a flat surface, regardless of whether the surface is parallel with the focal plane of the imaging instrument.

A maximum intensity rendering can be performed with standard software packages for three-dimensional image analysis.

In the optional fifth step of the invention steps 3 and 4 can be repeated to obtain additional images of the surface morphology within the area that the compound was applied to. This may be desirable if the size of the area that is imaged in step 3 is much smaller than the area that the compound (e.g., fluorescent dye) is applied to, for example to study whether there are any variations in the surface intercellular and intracellular structure within this area.

Methodology

Equipment

Stacks of fluorescence as well as reflectance images were taken with a Noran In Vivo OZ scanning confocal microscope. Maximum intensity renderings of the stacks of images were performed with the image analysis software supplied with the instrument.

Experimental procedure

A contrast enhancing fluorescent dye, fluorescein, was applied topically by soaking a circular area of the skin, 0.5" in diameter, for two minutes with 200 μl of an aqueous solution at a concentration of 1,000 ppm and a pH of 7.0. The skin was subsequently rinsed with tap water for 10 seconds and patted dry. Images were subsequently acquired with the in vivo confocal microscope.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLE 1

Contrasting Clarity of Image Using Fluorescence Versus Reflectance

FIG. 1 is a photograph of two images of the exact same area of the skin surface, approximately 0.1×0.1" in size, of a subject, one image in reflectance, the other in fluorescence after the application of fluorescein. The heterogeneous absorption of the fluorescent dye clearly yields a degree of contrast superior to the reflectance image, where contrast arises from variations in refractive index.

EXAMPLE 2

Figure 2:
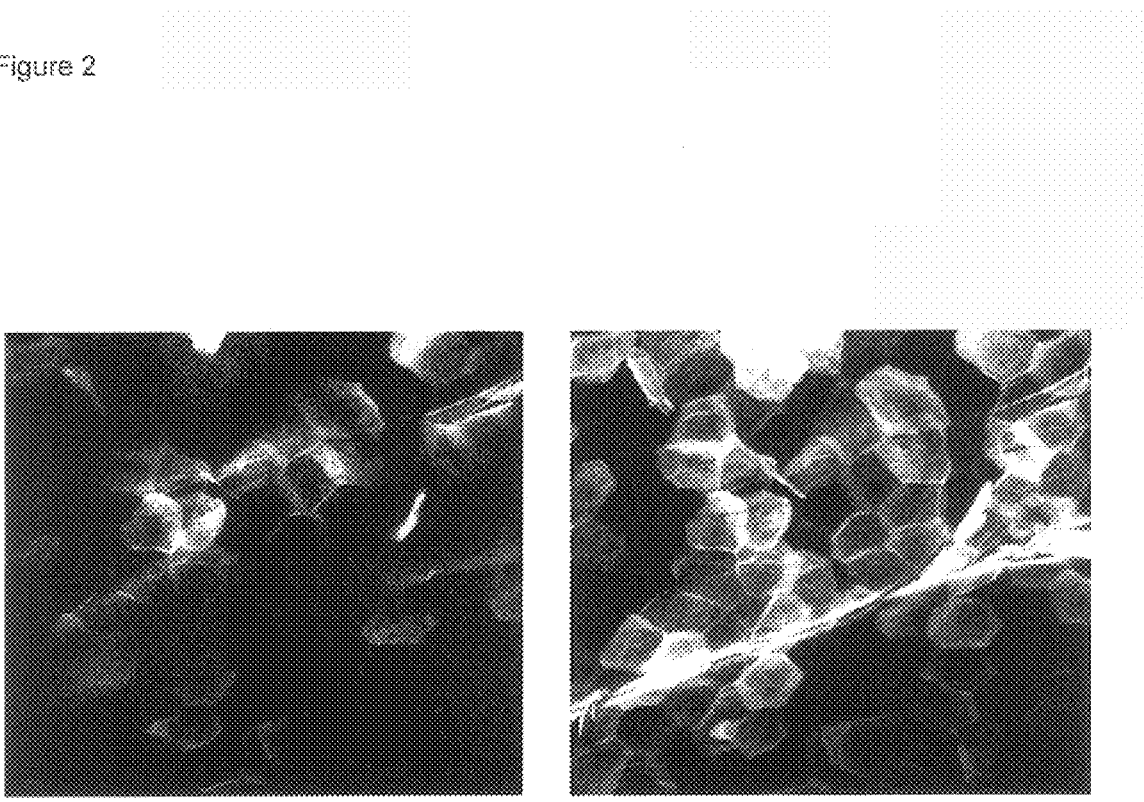
Figure 3:
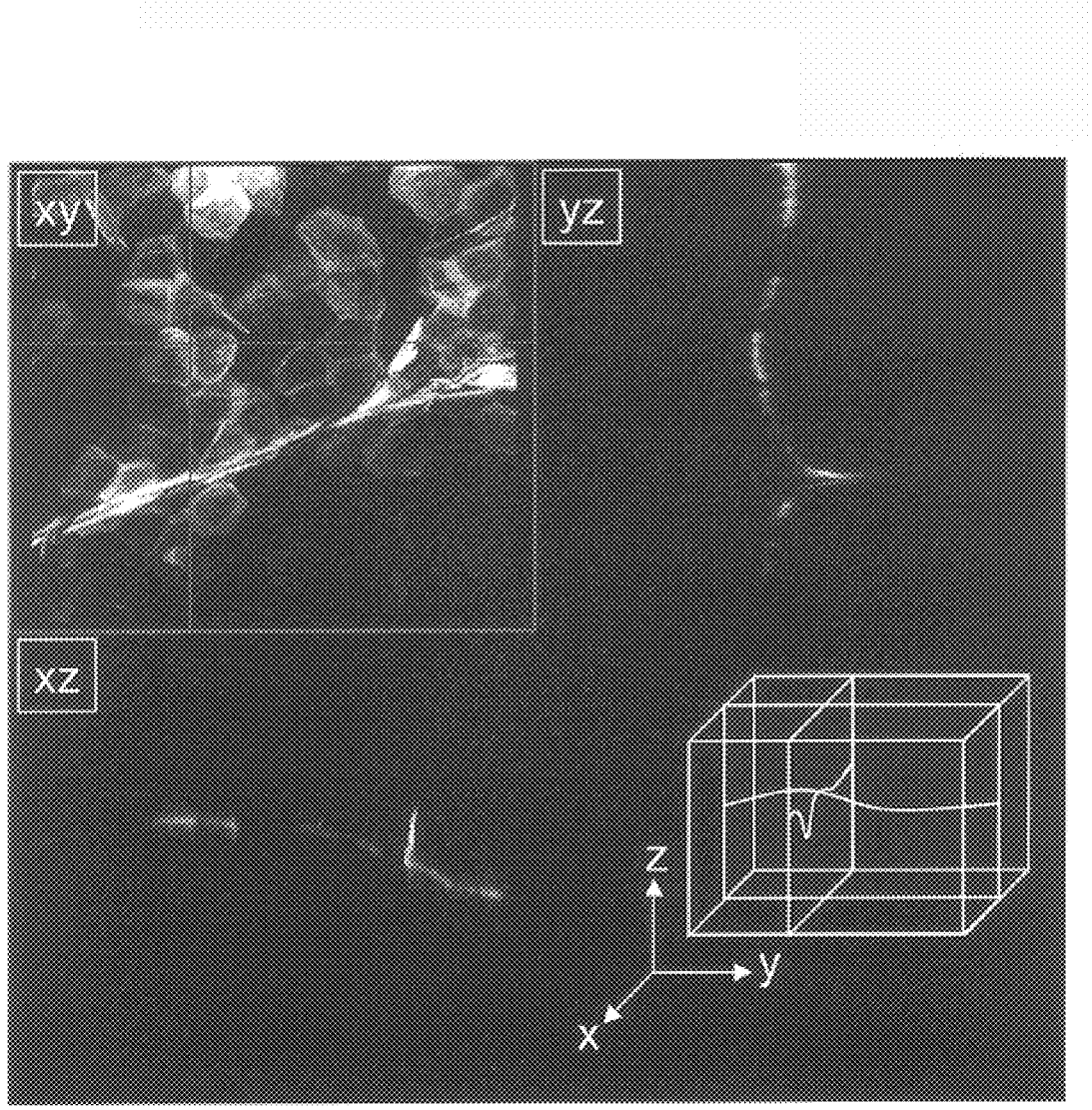

Comparing a Single Image from a Stack of Images Taken of a Textured Surface to the Maximum Intensity Rendering FIG. 2 is a schematic representation of two images. The image on the left represents a single image taken from a skin surface exhibiting significant surface texture. The degree of texture is shown in FIG. 3, which displays vertical cross sections in the xz- and yz-plane of the same stack of fluorescence images. The single image in FIG. 2 clearly shows only certain cells in focus. These are the cells that coincided with the focal plane of the microscope objective when the image was taken. The dark areas in the image correspond to the surface cells that were either above or below the focal plane of the objective. The image on the right in FIG. 2 is the result of a maximum intensity rendering of the stack of images that the image on the left was taken from. Clearly, in the rendered image all the surface cells appear in focus, and a clear view of the intercellular and intracellular structure of the skin surface is obtained.

EXAMPLE 3

Imaging Intracellular Features

Figure 4:
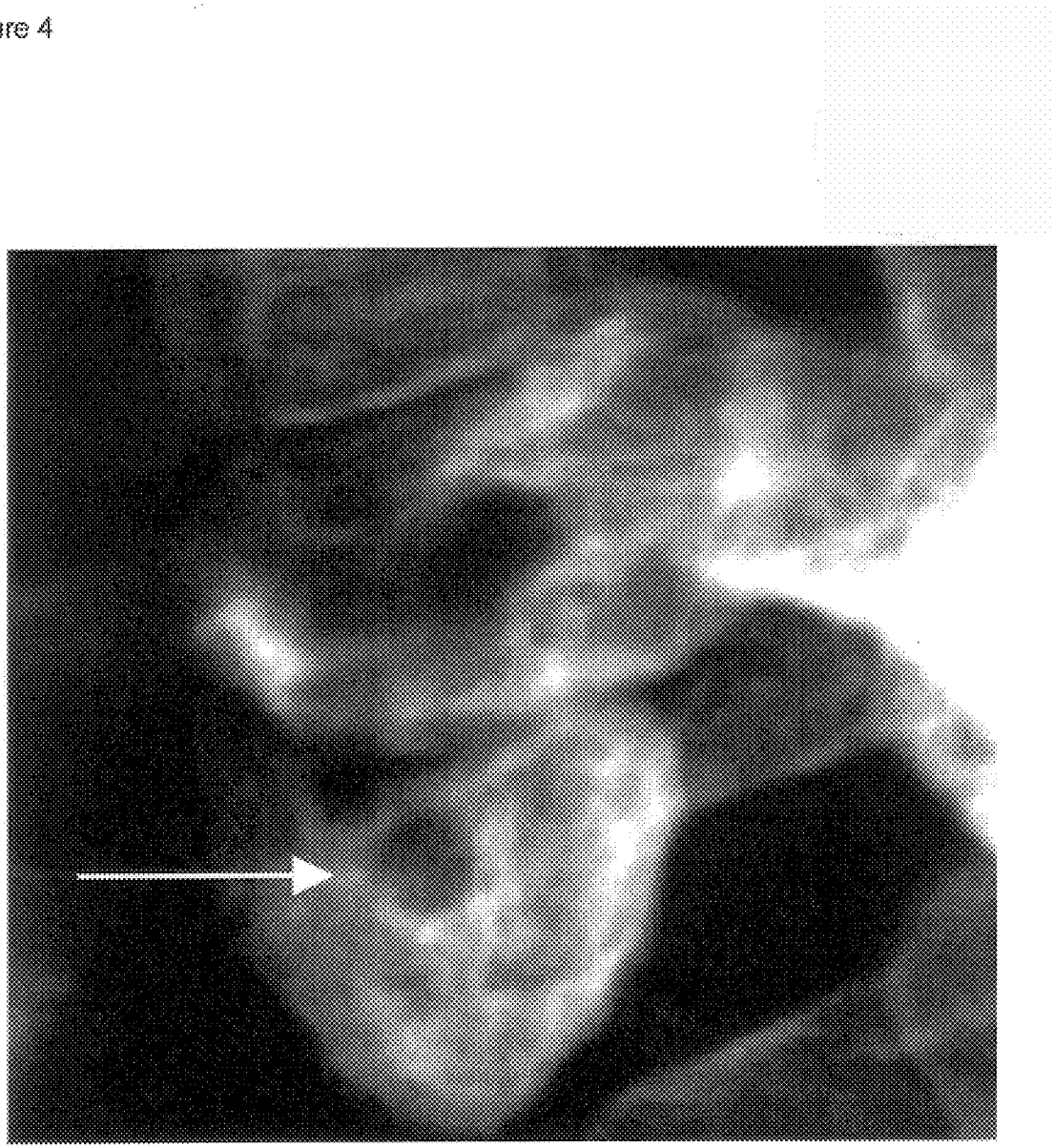
FIG. 4 shows an example of enhanced intracellular contrast resulting from topical application of fluorescein.

FIG. 4 shows an example where the fluorescent dye enhances contrast within single cells. The arrow points towards a distinct roundly shaped feature, possibly the remnants of the cell's nucleus.

What is claimed is:

1. A method for imaging the intercellular and intracellular structure of a skin surface comprising:

(1) choosing a desired site of any desired size or shape on the subject's body;

(2) topically applying a contrast enhancing compound, which compound absorbs heterogeneously at the skin surface, to the chosen site on the surface of the skin using any suitable application method;

(3) acquiring a single image which focuses all skin cells on said skin surface if the skin is within the focal plane of the imaging instrument used or optionally acquiring multiple images if the skin surface is not within the focal plane of the imaging instrument used, by any suitable method, of an area that is contained within the site that the compound was applied to;

(4) if the skin surface area that is imaged is not within the focal plane of the imaging instrument, reconstructing the multiple images into a single image that displays all cells on the skin surface in focus by performing a maximum intensity rendering;

(5) optionally repeating steps (3) and (4) to collect additional images as required.

2. A method according to claim 1, which is an in vivo method.

3. A method according to claim 1, wherein said compound is a fluorescent dye.

4. A method according to claim 3, wherein said dye is selected from the group comprising of fluorescein, pyranine and fluorescein octadecyl ester.

5. A method according to claim 1 wherein, if maximum intensity rendering is performed, compound or compounds are predominantly absorbed in the uppermost layer of skin cells.

6. A method according to claim 1, wherein area over which images is acquired is 10–40 μm.

* * * * *